United States Patent [19]

Herrera

[11] Patent Number: 4,848,572
[45] Date of Patent: Jul. 18, 1989

[54] FEMININE HYGIENE DEVICE

[76] Inventor: Patricio B. Herrera, Junin 116, Barrio "San Marcos", Quito, Ecuador

[21] Appl. No.: 58,214

[22] Filed: Jun. 4, 1987

[30] Foreign Application Priority Data

Jun. 9, 1986 [EC] Ecuador .............................. SP-86-183

[51] Int. Cl.$^4$ .............................................. A61B 17/06
[52] U.S. Cl. ..................................... 206/440; 206/438; 206/363; 604/358; 604/386
[58] Field of Search ............... 206/204, 210, 363, 438, 206/440, 441, 812; 604/358, 360, 386, 403, 400

[56] References Cited

U.S. PATENT DOCUMENTS

| | | |
|---|---|---|
| 1,608,934 | 11/1926 | Goldsmith . |
| 2,066,946 | 1/1937 | Reiman . |
| 2,102,858 | 12/1937 | Schlumbohm . |
| 2,125,620 | 8/1938 | Schlumbohm . |
| 2,523,323 | 9/1950 | Privott . |
| 2,637,439 | 5/1953 | Banks . |
| 2,742,042 | 4/1956 | Flanders ............................ 604/359 |
| 2,834,459 | 5/1958 | Rickard et al. ..................... 206/440 |
| 2,841,147 | 7/1958 | McLaurin . |
| 2,940,449 | 6/1960 | Thomson . |
| 2,952,354 | 9/1960 | Whitelaw et al. . |
| 3,004,895 | 10/1961 | Schwartz ............................ 604/360 |
| 3,035,578 | 5/1962 | Elmore ............................... 206/440 |
| 3,150,049 | 9/1964 | Emory . |
| 3,534,887 | 10/1987 | Ginsberg . |
| 3,561,456 | 2/1971 | Stuart, Jr. . |
| 3,618,756 | 11/1971 | Trewella ............................ 206/440 |
| 3,635,567 | 1/1972 | Richardson, Jr. . |
| 3,698,549 | 10/1972 | Glassman ........................... 206/440 |
| 3,875,942 | 4/1975 | Roberts et al. ..................... 604/359 |
| 3,889,804 | 6/1975 | Ravich . |
| 3,905,372 | 9/1975 | Denkinger ......................... 604/360 |
| 3,926,309 | 12/1975 | Center . |
| 3,973,567 | 8/1976 | Srinivasan et al. ................ 206/440 |
| 4,182,336 | 1/1980 | Black ................................. 206/438 |
| 4,190,154 | 2/1980 | Clark . |
| 4,195,634 | 4/1980 | Disalvo et al. ..................... 604/359 |
| 4,221,221 | 9/1980 | Ehrlich . |
| 4,417,894 | 11/1983 | Norris . |
| 4,420,080 | 12/1983 | Nakamura . |
| 4,428,477 | 1/1984 | Cristofolo . |
| 4,437,567 | 3/1984 | Teng ................................. 206/210 |
| 4,522,302 | 6/1985 | Paikoff . |
| 4,523,679 | 6/1985 | Paikoff . |
| 4,610,357 | 9/1986 | Nakamura . |
| 4,651,874 | 3/1987 | Nakamura . |
| 4,685,909 | 8/1987 | Berg et al. ......................... 604/360 |
| 4,702,378 | 10/1987 | Finkel et al. . |

Primary Examiner—David T. Fidei
Attorney, Agent, or Firm—Cushman, Darby & Cushman

[57] ABSTRACT

A sanitary napkin device includes a sanitary napkin having a curved, trapezio-pyramidal shape closely complementary to the female anatomy and a towelette hermetically sealed in an elongate sheath releasably attached to an impermeable member of the sanitary napkin by an adhesive strip extending longitudinally of the sanitary napkin. The towelette contains an aseptic solution which helps clean the female genital area and leaves a coating for preventing the proliferation of undesirable organisms.

15 Claims, 5 Drawing Sheets

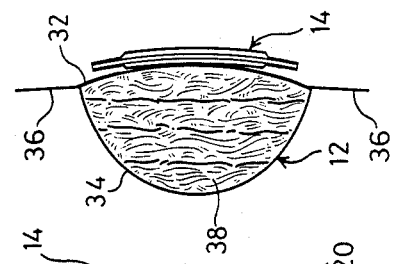
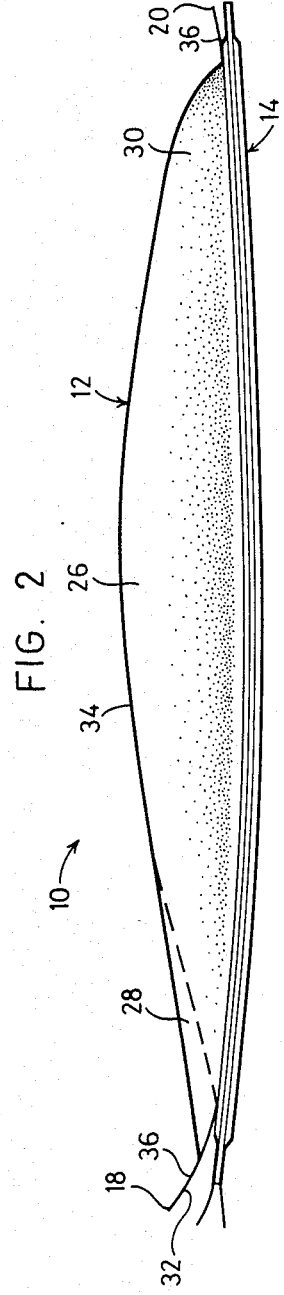
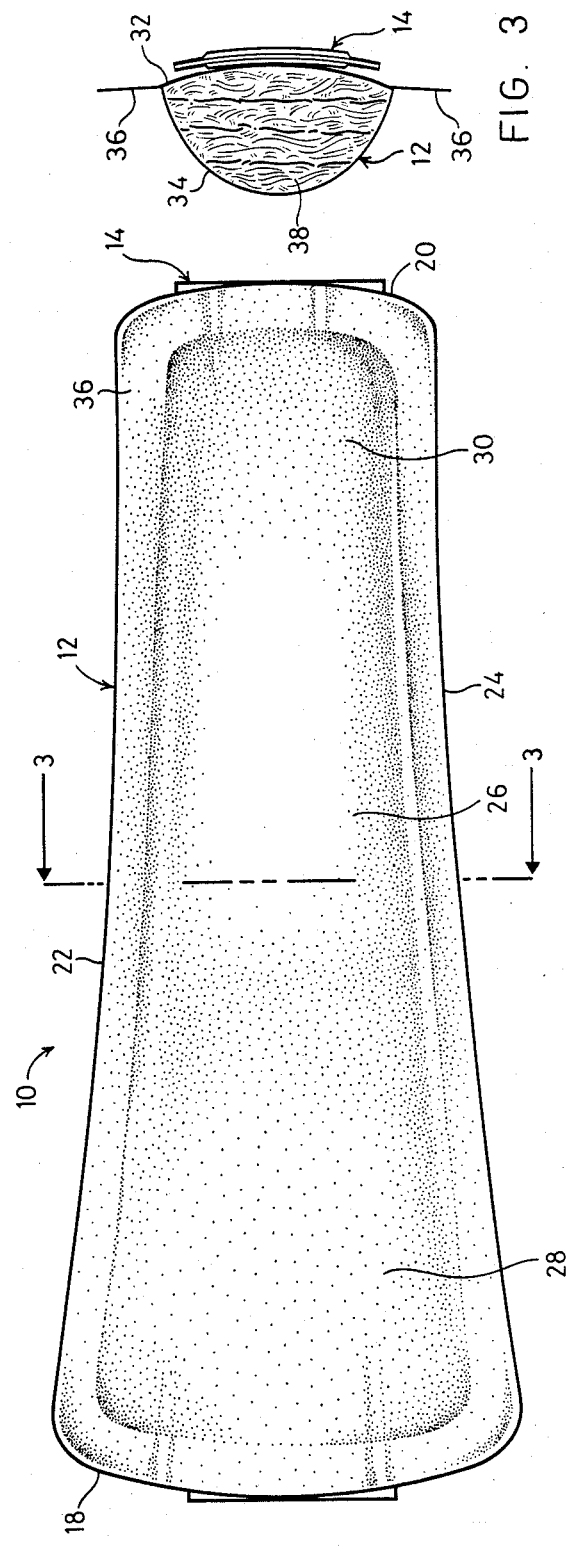

FEMININE HYGIENE DEVICE

BACKGROUND OF THE INVENTION

The present invention relates to feminine hygiene, and, more particularly, to disposable sanitary napkins provided with adhesive so that the napkin can be releasably secured to an undergarment of the user. Typically, a piece of siliconed paper tape is provided to cover the adhesive prior to use, and, thereby, prevent the adhesive from sticking to anything before it is desired to put the sanitary napkin to use. Such a sanitary napkin is limited since it merely provides a structure for absorbing excess discharge, and has no structure for cleaning or asepticizing the area of the female genitalia prior to placement of the sanitary napkin.

SUMMARY OF THE INVENTION

By the present invention, a self-adhesive disposable sanitary napkin device is provided which not only includes a sanitary napkin which may be secured to undergarments to absorb discharge, but also includes structural elements which serve to externally clean and asepticize the feminine genitals and surrounding areas and to leave an aseptic coating which provides a pleasant sensation. Such a provision for cleaning, and thereby preventing the proliferation of undesirable organisms, is especially important at times or in places in which no other manner of cleaning the affected areas is available.

In order to provide the advantages described above, the sanitary napkin device according to the present invention includes a sanitary napkin having an exterior permeable cover of disposable material, an extra-absorbent interior pad, an impermeable exterior protector, and an adhesive strip secured to the exterior protector. The sanitary napkin device also includes a hermetically sealed sheath adhered to the adhesive strip, isolating the adhesive strip prior to use, and, sealed in the hermetic sheath, a towelette containing an aseptic material. The sheath also serves to reinforce the sanitary napkin, preventing deformation of the napkin during packaging and shipping and when the napkin is in the possession of the consumer prior to use, a function not served by the thin paper strips covering the adhesive strips of some known sanitary napkins.

In use, the hermetic sheath is opened, the aseptic towelette is extracted and used to wipe the genital area to be cleansed. The empty sheath is pulled away from the impermeable exterior protector to expose the adhesive, and the sanitary napkin is placed over the pre-asepticized area. The adhesive strip is then adhered to an interior surface of an undergarment.

The sanitary napkin has: a thick, voluminous orthocentral portion; a narrow portion, which is slightly narrower and slightly thinner than the orthocentral portion and curves somewhat with respect to the orthocentral portion so that the sanitary napkin tends to be concave along its length; and a voluminous portion which is wider and thinner than the other portions of the sanitary napkin and curved more than the narrow portion. This shape of the sanitary napkin is closely complementary to the shape of the female genital area, the lengthwise concavity of the sanitary napkin conforming to the generally convex shape of the female anatomy, and the transverse convexity of the sanitary napkin conforming to the transverse concavity of the vulvar groove. In addition, the transverse convexity of the sanitary napkin is modified by the transverse forces exerted on the sanitary napkin by the lower limbs molding the sanitary napkin to the particular requirements of the vulvar groove of the wearer.

BRIEF DESCRIPTION OF THE DRAWINGS

FIG. 1 is a top plan view of the sanitary napkin according to the present invention;

FIG. 2 is a front elevation of the sanitary napkin of FIG. 1;

FIG. 3 is a cross-section taken along the line 3—3 in FIG. 1;

DETAILED DESCRIPTION OF THE PREFERRED EMBODIMENT

Figure 4:
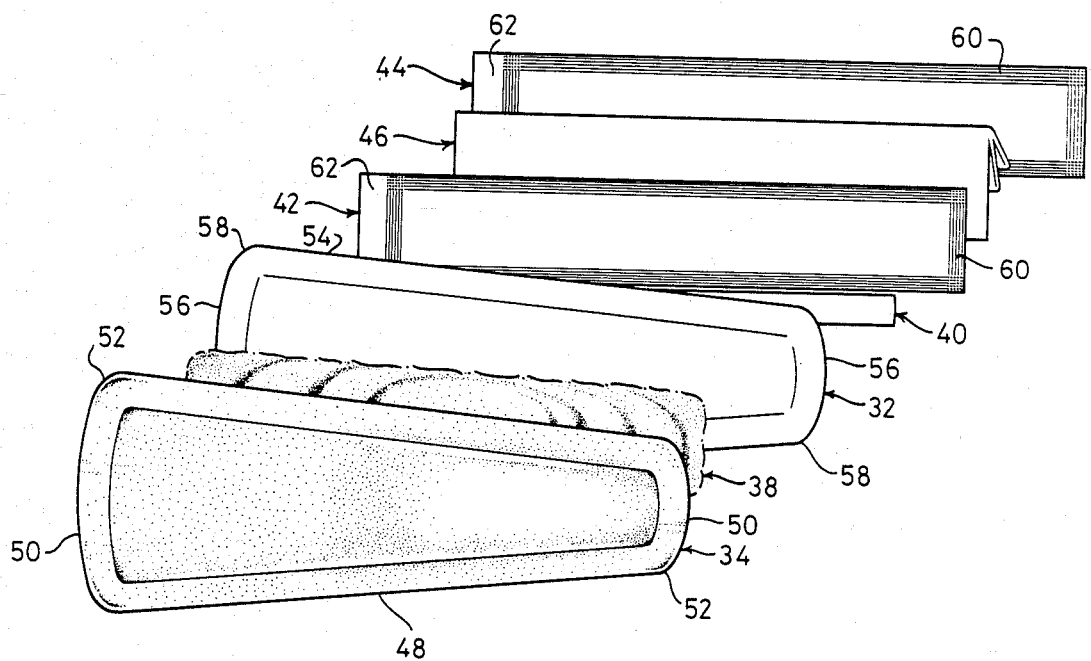
FIG. 4 is an exploded view of the sanitary napkin of FIG. 1.

As can best be seen from FIGS. 1 and 2, the aseptic self-adhesive disposable sanitary napkin device according to the present invention, which is designated generally by the reference numeral 10, includes a sanitary napkin 12 and a hermetically sealed sheath 14 containing a towelette 16 (see FIG. 4) moistened with an aseptic liquid. The sanitary napkin 12 has a generally trapezoidal shape in plan view, having a wide end 18 and a narrow end 20 across the width of the napkin 12, the ends 18 and 20 being generally parallel to one another but curving slightly outward from one another. The sides 22 and 24 of the sanitary napkin 12, which are nonparallel with respect to one another, curve slightly toward one another. The sanitary napkin 12 has a height, or one another. The sanitary napkin 12 has a height, or thickness, which varies from a maximum near the longitudinal center of the napkin to a minimum at the wide end 18. The sanitary napkin 12 has a voluminous and thick orthocentral portion 26, a narrow portion 28 adjacent to the narrow end 20, and a wide portion 30 adjacent to the wide end 18. The volume and thickness of the sanitary napkin 12 slowly diminish from the orthocentral portion through the narrow portion 28, and then diminish abruptly at the narrow end 20. The volume at the wide portion 30 of the sanitary napkin 12, in spite of the fact that the volume is approximately equal to the volume of the narrow portion 28, decreases more immediately from the orthocentral portion 26 and continuously decreases in thickness until it finally becomes very thin near the wide end 18.

A bottom surface of the sanitary napkin 12, which is defined by an exterior impermeable protector 32, is slightly concave upward along its length, as can be seen from FIG. 2, and the concavity increases when the hermetically sealed sheath 14 is separated from the napkin. As can be seen from the cross-section of FIG. 3, a top surface of the napkin 12, which is defined by a permeable exterior cover 34, defines an arc covering approximately 180 degrees transversely from a pair of longitudinal flanges, which are part of a peripheral region 36 of attachment, and the bottom surface of the napkin 12 bows slightly downward from a plane containing the flanges.

As can be seen from FIG. 4, the sanitary napkin comprises the permeable exterior cover 34, an interior pad 38, the exterior impermeable protector 32 and a self-adhesive strip 40. The sheath 14 includes two sheets 42 and 44 of material, each comprising a plurality of layers, and a folded towelette 46 moistened with an aseptic solution is hermetically sealed in the sheath. The permeable exterior cover 34 is made of a disposable material, soft to the touch, and extremely absorbent, but at the same time, imperishable and very adaptable. The most suitable material is a cloth of 16 to 24 grams per square meter. The permeable exterior cover 34 has an elongated trapezoidal form with slightly convex sides 48 and ends 50 and very rounded vertices 52. The sides 48 are slightly concave when the cover 34 is secured to the other parts of the sanitary napkin 12, as shown in FIG. 1, but are slightly convex when the cover 34 is in its relaxed, unassembled condition, as can be seen from FIG. 6. Suitable dimensions for the permeable exterior cover 34 are: total length at the midline—195.00 mm; width at the midpoint—80.00 mm; width at the wide end—85.00 mm; and width at the narrow end—65.00 mm.

The exterior impermeable protector 32, to which the permeable exterior cover 34 is connected and with which the permeable exterior cover 34 forms a pouch for the interior pad 38, has sides 54 which are basically rectilinear and ends 56 which are slightly curved, thereby leaving vertices 58 which are completely convex. The impermeable protector 32 is secured to the permeable cover 34 along all sides and ends by, for example, heat sealing to define the region 36 of attachment in the form of a strip or flange, the width of the flange and, therefore, the width of the region 36 of attachment being approximately 10 mm around the periphery of the sanitary napkin 12.

The interior pad 38 is made of a highly absorbent material, such as cellulose, and is compressed as a filling between the exterior permeable cover 34 and the exterior impermeable protector 32, whereby the sanitary napkin 12 takes on its characteristic trapezio-pyramidal shape. The pad 38 is very voluminous from the orthocentric portion 26 of the sanitary napkin 12 toward the narrow end 20. In contrast, the volume of the pad 38 slowly decreases as it approaches the wide end 18, at which the pad 38 becomes very thin. The dimensions of the pad 38 vary in accordance with the dimensions of the sanitary napkin 12, but typical, suitable dimensions can be as follows: total length at the midline—170.00 mm (+/−10 mm); width at the midpoint—40.00 mm (+/−2 mm); width at the wide end—50.00 mm (+/−3 mm); width at the narrow end—30.00 mm (+/−1 mm); thickness at the orthocenter—20.00 mm (+/−5 mm); thickness at the narrow end—10.00 mm (+/−3 mm); and thickness at the wide end—5.00 mm (+/−1 mm).

The exterior impermeable protector 32 is a thin, stable, and highly flexible layer having a stamped weft and warp pattern which increases resistance to spontaneous deformation, without sacrificing the needed degree of flexibility. Polyethylene is a suitable material for the external impermeable protector 32. The basic function of the protector 32 is to impede genital fluids, which are especially abundant during menstruation and which are collected in the pad 38, from contaminating clothing. Suitable dimensions for the protector 32 for use with the permeable cover 34 and the pad 38 whose dimensions have already been given are: total length at the midline—205.00 mm; width at the midpoint—67.50 mm; width at the wide end—80.00 mm; and width at the narrow end—55.00 mm.

The self-adhesive strip 40 comprises a thin film having an adhesive on both sides. The strip is preferably long and narrow and attached to the exterior surface of the exterior impermeable protector 32 longitudinally along the midline of the protector. The strip can be rectangular having, for example, a length of 205.00 mm and a width of 10.00 mm. When one side of the adhesive strip 40 is adhered to the protector 32, the opposite side is exposed to secure the hermetic sheath 14 for housing the aseptic towelette 46.

Because the peripheral area of the sanitary napkin 12 is heat sealed, it shrinks slightly, exercising additional constrictive forces which cause the concave arch along the length of the sanitary napkin, with the wide portion 30 being the most affected. The narrow portion 30 is less affected and the orthocentric portion 26 does not yield to these forces, but remains parallel with respect to the horizontal, that is, parallel to the plane occupied by the sanitary napkin 12 prior to heat sealing. The constrictive forces generate in the sanitary napkin 12 a warp congruent to the external anatomy of the female genitalia. The napkin so arched does not exceed 20 mm of thickness at its predominant point. However, this real thickness, which corresponds to a constant volume of pad 38 or filling, is capable of varying more or less between approximate limits, which are from 10 to 40 mm maximum at the thickest point, which is the orthocentral portion 26. This variability in thickness increases or decreases according to the magnitude and direction of the compressive forces which are exercised o the sanitary napkin 12 during use. The thickness increases when the napkin 12 is transversely gripped and the edges of the sides 22 and 24 are compressed in unison; and the thickness can be reduced, compacting the pad 38 even more, when the napkin is gripped by the permeable cover 34 and the impermeable protector 32, since the cover and the base, in and of themselves, compress the pad 38. The thickness may also vary, especially at the orthocentric portion 26, upon increasing or decreasing the arch which the napkin naturally defines. The constrictive and compressive forces and the pyramidal form of the sanitary napkin 12 over the trapezoidal protector 32 determine the unequal distribution of the material in the pad 38, which makes it easy to define for descriptive purposes, the orthocentric portion 26, the narrow portion 30 and the wide section 28 of the sanitary napkin 12.

The orthocentric portion 26 is the most prominent of the three portions and corresponds to the apex of a chamber which encloses the pad 38. Thus, the orthocentric portion 26 is the bulkiest and thickest portion of the sanitary napkin 12, located precisely in the orthocenter of the napkin between the other two portions 28 and 30, with which the orthocentric portion defines an indivisible and uniform body. The orthocentric portion 26 is more resistant to the action of the constrictive forces on the napkin 12, so that the base of the orthocentric portion 26, which is the protector 32, remains parallel to the horizontal, or originally occupied, plane even though the protector 32 spontaneously bends transversely due to the compression exercised on it by the permeable cover 34 acting through the pad 38.

The narrow portion 30 begins in an area near the orthocentric portion 26 and ends at the narrow end 20 of the sanitary napkin 12, where the narrow portion 30 is moderately warped. The volume of the pad 38 is less in the narrow portion 30 than in the orthocentric portion 26 due to the fact that the thickness of the pad 38 decreases.

The wide portion 28 is very flexible and comfortable and is the widest, thinnest and most warped portion of the sanitary napkin 12. The volume of the pad 38 in the wide portion 28, which is approximately equal to the volume of the pad 38 in the narrow portion 30, is diffused along the length and width of the wide portion 28 and, therefore, its thickness slowly decreases until it becomes flat, in contrast to the narrow portion 28 whose thickness diminishes, but without becoming flat. This quality of maximum width and minimum thickness in the wide portion 28 allows the constrictive forces to act more effectively, gradually warping this, the widest part of the sanitary napkin, from the orthocentric portion 26 to the wide end 18.

Figure 5:
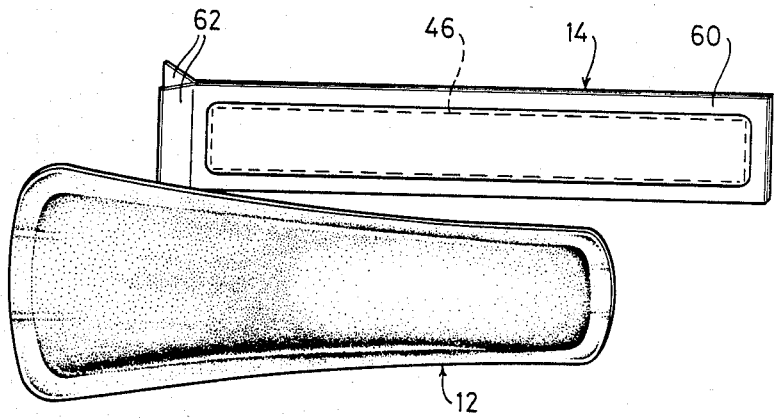
FIG. 5 is a view similar to FIG. 1, but showing the hermetic sheath separated from the remainder of the sanitary napkin.

The two sheets 42 and 44 of material of the sheath 14 are elongate rectangular sheets which are heat sealed along all four sides to define a hermetically sealed chamber for the towelette 46. Each sheet 42 and 44 comprises a plurality of layers including, from the inside out, a polyethylene layer, an aluminum layer, a paper layer and a silicone layer, which is the exterior covering. The thickness of each layer is typically 150+/−50 microns. Due to its undegradable chemical and physical properties, the polyethylene layer serves to provide an impermeable barrier between the aluminum and towelette 46, creating an adequate and enduring sterile environment for the towelette. The aluminum and paper layers are consolidated into a combined layer of aluminum/paper complex to define a layer of armor protecting the towelette 46 against the chemical and physical agents of the environment. The light covering of silicone repels environmental humidity and reduces the natural adhesivity of the paper and, thereby, facilitates the removal of the sheath 14 from the self-adhesive strip 40, the sheath 14 being shown separated from the sanitary napkin 12 in FIG. 5. By "silicone" is meant silicones or organopolysiloxanes, which are pharmacologically inert, non-toxic synthetic polymers consisting of alternating chains of silicone and oxygen atoms bonded to organic groups. They are widely used in medicine, especially in dermatology. The sheath 14 also protects the self-adhesive strip 40 by isolating the strip from the environment until the moment of its fixation to another surface.

An area 60 of heat sealing occupies, for example, a 5 mm strip of surface along each side of the sheath 14. At one end of the sheath 14, flaps 62 of, for example, 10 mm extend beyond the heat sealing area 60 and can be gripped by the fingers to separate one sheet 42 of the sheath 14 from the other sheet 44, by which the sheath 14 is opened to allow the extraction of the towelette 46.

The towelette 46 is made of a thin, hydrophilic, very delicate, disposable cloth material having a regular form. For example, the cloth can be rectangular having dimensions of 18.0 cm by 16.5 cm and can weigh 16 to 24 grams per square meter. The material does not leave behind residues, due to the fact that it is a tissue manufactured by the simultaneous fiber impregnation system, and is not conducive to microorganic life. The towelette 46 can be made up of one, two or more sheets of the selected material. When rubbed over the skin, the towelette 46 dislodges and collects among its absorbent fibers the mephitic and unhealthy residues which should be eliminated.

The towelette 46 contains an oily topical solution having a specific weight of, for example, between 1.00 and 1.03, very similar to water, which makes the topical solution extremely fluid and very light. This physical quality permits the topical solution to be diffused without complications and to clean areas which are difficult to reach. The solution typically includes a 30% solution of a hydrosoluble base, such as a propylene glycol, in water, purified water being the only excipient. The solution is chemically inert, sterile, odoriferous or non-odoriferous, aseptic, non-antiseptic, nonmedicated, non-disinfectant, non-germicidal, nonbactericidal, non-fungicidal, and free of other natural or artificial substances which are potentially sensitizing.

The propylene glycol always has a lower osmotic pressure than that of the porous skin layer, pilose follicles and external mucous membranes and, therefore, has adsorption capacity. This physical property allows for a light impregnation of the epithelium and pilose follicles without the possibility of being assimilated into the tissue structure. In addition, propylene glycol is a cutaneous detergent (which cleanses and purifies) since it is prepared for the action of hypochlorous acid on the propylene, followed by saponification. Due to its oily nature, the evaporation of the solution is near zero, so that it leaves a very fine layer on the epidermis and pilose follicles, thereby preventing further secretions from accumulating. More specifically, at the same time that propylene glycol maintains the wiped areas moist, it repels the normal endogenous and exogenous impurities, has a protective barrier action which counter-arrests the action of irritating chemicals (soap residues, ammonia resulting from the decomposition of urine, especially in nursing mothers, intimate deodorants, menstrual deposits in a constant process of decomposition, etc.), and reduces the severity of products which dehydrate the cutaneous surface (sanitary napkins, disposable diapers, non-disposable diapers, talcum powders, toilet paper, etc.). It also protects against the physical environment (heat, cold, wind, humidity and dryness), dust, foreign organic particles such as cotton or wool residues, and the rubbing of the skin on rough and/or drying surfaces. It is a barrier substance which has been used for generations for counter-arresting minor dermatological diseases because it calms burning and itching. In addition, the solution facilitates the removal of dried excretions. This topical solution does not contain antiseptic products or medicated substances, either dissolved or in any other form, since its objective is to prevent problems and promote health rather than to cure problems. Thus, the treated towelette 46 provides a mechanism for cleaning and asepticizing the skin, pilose follicles and, principally, the external mucous membranes: uro-genitals and digestive organs (external anal sphincter and adjacent cutaneous portions) in order to prevent disease and promote health.

The chemical composition of the topical solution utilizes known substances which comply with the conditions imposed by pharmaceutical science and by experts from the World Health Organization. The topical solution can contain, as soluble substances, aromatic substances for the interchange of odors in the area, replacing the disagreeable ones with delicate fragrances, and it also may contain a biological preservative which improves the sterility of the system. The aromatic substances and the biological preservative can be dissolved in an aqueous excipient which is innocuous. The topical solution has a pH between 6.5 and 8.5, which makes it isotonic with the vaginal mucous membranes. Due to this characteristic, the application of the topical solution does not cause problems or cause side effects because it is in equilibrium and within the pH limits determined by the very humor of the involved area. The towelette 46 is wetted with $1.50 +/- 0.50$ ml of solution per decimeter of towelette. In general, 1 ml per square decimeter is the normally used quantity. The topical solution is measured in order to avoid exaggerated wetting of the area of application and to make the oily towelette 46 easy to handle. The topical solution has an immediate and prolonged action which provides a comfortable sensation, in turn inducing a positive psychological feeling of security. The topical solution can be totally removed from the area of application by simply wiping the area with a dry towel or by washing it.

The sheath 14, which is not more than 3 mm in thickness, provides a more rigid and stable support for the sanitary napkin 12 than does the silicon covered piece of paper which is conventionally used to cover an adhesive strip. Therefore, the sheath 14 aids in maintaining the trapezio-pyramidal structure of the sanitary napkin 12 until the sanitary napkin device 10 is utilized, thereby impeding deformations caused by handling during final packaging and transporting, both on a factory level and on a consumer level.

The sanitary napkin 12 according to the present invention assures a rigorous joining and excellent conforming with the feminine genital area for at least two reasons: the asymmetric concave warp of the sanitary napkin 12 is congruent to the external anatomy, and the thickness of the pad 38 is variable due to the external forces produced by the location of the sanitary napkin 12 relative to the body. The concave warp is important because it provides an arch structure which expedites the spontaneous union of the sanitary napkin 12 with the generally convex shape of the female anatomy, especially the pubis. The sanitary napkin 12 is transversely compressed at its lateral edges by the musculature of the parts of the body near the genitalia, principally the muscles at the internal route of the lower limbs. This action causes the pad 38 to mold itself to the anatomical requirements of the vulvar groove, which is specific to each woman, gaining thickness at the expense of reducing width in the affected areas of the sanitary napkin 12 and maintaining a stable volume of pad. The proper placement of the sanitary napkin 12 is important because the proper functioning of the sanitary napkin, the capturing of the menstrual fluid and its assimilation by the orthocentric portion 26, and then its accumulation, more in the narrow portion 30 than in the wide portion 28, depends upon proper placement. The orthocentric portion 26, the most prominent part of the sanitary napkin 12, must be adjusted to the area around the vaginal orifice, with the narrow portion 30 oriented towards the back. This narrow portion 30, in spite of the fact that it contains the same volume of pad 38 as the wide portion 28, always accumulates more fluid than the wide portion 28 because the narrow portion 30 constitutes the lowest and most compacted portion of the sanitary napkin 12. This peculiarity in the design of the sanitary napkin 12 and its correct orientation allow the disbursement of the fluid to be controlled and reduce, in a way, the inevitable adherence of menstrual residues, especially abundant in the area adjoining the genitals. The thin, wide and very warped characteristic of the wide portion 28, because it thins down especially near the edges and the wide end 18, permits the sanitary napkin 12 to very discreetly cover the pubescence, avoiding the unaesthetic bulkiness normally present in other sanitary napkins. In addition, the firm union established between the self-adhesive strip 40 and the undergarment ensures the stable immobility of the sanitary napkin 12, and, at the same time, facilitates the generation of additional compressive forces from the undergarment. These forces push the warped body of the napkin 12 against the convex genital anatomy, hence causing the total joining and adaptation of the sanitary napkin to the corporal peculiarities of each woman.

Figure 6:
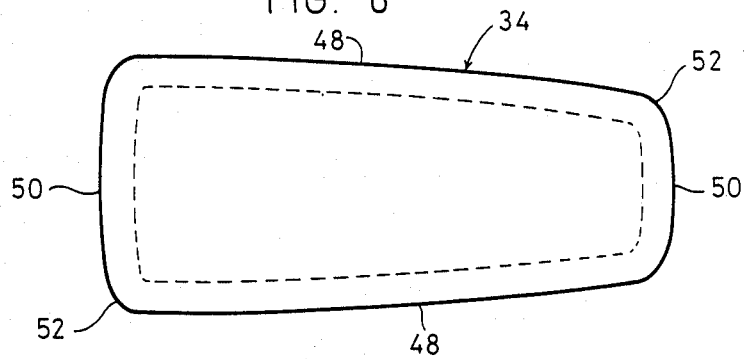
FIG. 6 is a plan view of the exterior permeable cover.
Figure 7:
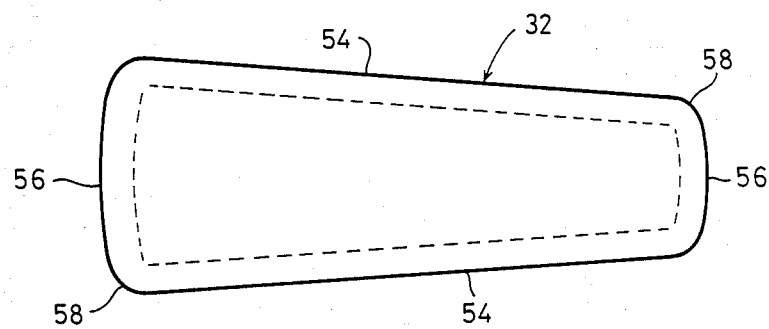
FIG. 7 is a plan view of the exterior impermeable protector prior to attachment to the sanitary napkin.
Figure 8:
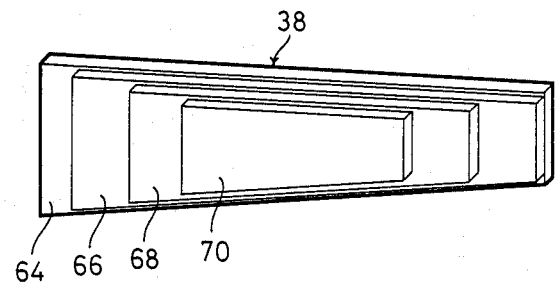
FIG. 8 is a perspective view of the interior pad.

As can be seen from FIG. 6, when the exterior permeable cover 34 is in its relaxed condition, unattached to the impermeable external protector 32, it has a generally trapezoidal shape, but the sides 48 are slightly convex. In contrast, the sides 54 of impermeable external protector 32 are essentially straight when the protector 32 is in its relaxed, unattached condition, as is shown in FIG. 7. As can be seen from FIG. 8, the absorbent pad 38 includes a plurality of trapezoidal layers 64, 66, 6 and 70, the layers decreasing in area from the bottom of the pad 38 to the top and having a typical individual thickness of 2.5 mm.

Figure 9:
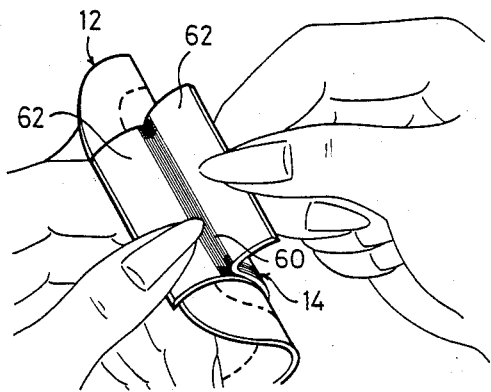
FIG. 9 illustrates a method for opening the hermetic sheath.
Figure 10:
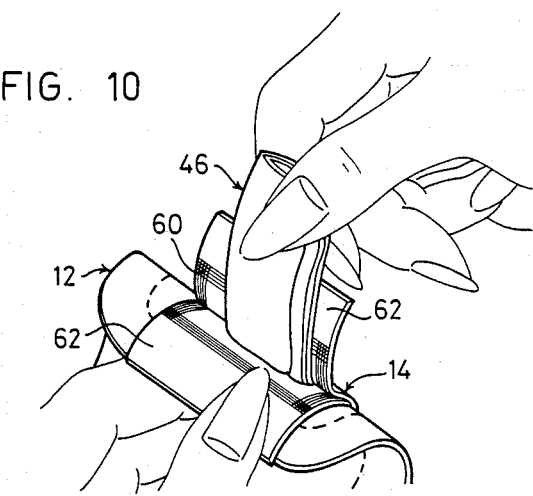
FIG. 10 illustrates a procedure for extracting the aseptic towelette.
Figure 11:
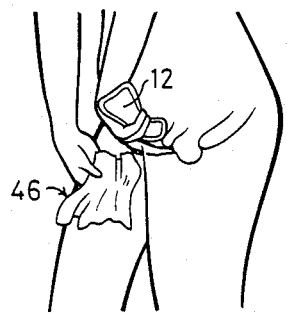
FIG. 11 illustrates a procedure for asepticizing using the aseptic towelette.
Figure 12:
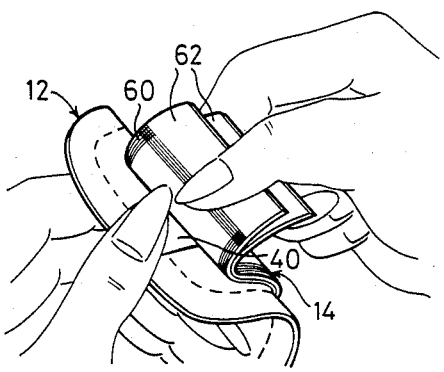
FIG. 12 shows the removal of the empty sheath from the self-adhesive strip of the sanitary napkin.

In use, the flaps 62 extending beyond the sealed area 60 of the sheath 14 are grasped, each between the thumb and forefinger of opposite hands and pulled apart, as shown in FIG. 9, to expose an end of the towelette 46. The towelette 46 is pulled from the sheath 14, as shown in FIG. 10, and used to wipe the residue from the genital area, as shown in FIG. 11, whereby it leaves a light, oily coating. The sheath 14 is separated from the sanitary napkin 12, as shown in FIG. 12, by grasping both flaps 62 between the thumb and forefinger of one hand and grasping the sanitary napkin 12 between the thumb and forefinger of the other hand and pulling apart to expose the adhesive strip 40 on the napkin 12.

Figure 13:
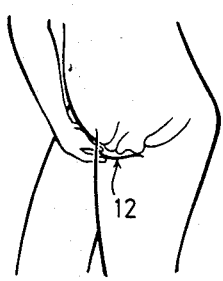
FIG. 13 illustrates a method of placing a sanitary napkin over the pre-asepticized area.
Figure 14:
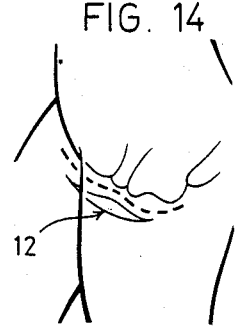
FIG. 14 is a schematic side view showing the congruence of the sanitary napkin with the external female genitals.
Figure 15:
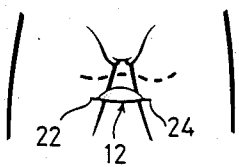
FIG. 15 is a schematic front view of the congruence of the transversely convex napkin with the transversely concave vulva.
Figure 16:
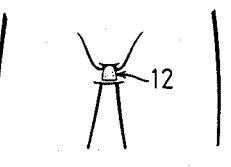
FIG. 16 is a schematic front view of the form and position assumed by the sanitary napkin when subjected to inherent extrinsic forces.
Figure 17:
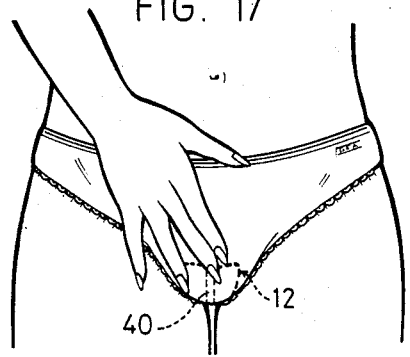
FIG. 17 shows the sanitary napkin according to the present invention in position and adhered to an undergarment.

The sheath 14 can be discarded, and the napkin 12 is placed in proper position in contact with the genitalia, as shown in FIG. 13, with the wide portion 28 in front, over the lower part of the pubescence, and the narrow portion 30 in back, passing the rear flank of the vulva. FIGS. 14 and 15 illustrate the generally complementary curvatures of the sanitary napkin 12 and the female anatomy, as seen from the side and front, respectively. The dashed line of FIG. 14 shows the correspondence of the concave longitudinal warp and the trapezoidal form of the sanitary napkin 12 with the anteroposterior convexity (wide in front and narrow in back) of the female genitalia. The dashed line of FIG. 15 confirms the congruence of the pyramidal structure (transversely convex) with the concave groove of the vulva. As can be seen from FIG. 16, the extrinsic forces generated from the internal routes of the thighs transversely compress the pad 38, forcing the pad 38 to adapt itself even more to the anatomical particularities of the groove of the vulva. FIG. 17 shows the self-adhesive strip 40 of the sanitary napkin being adhered to an internal surface of an undergarment.

It is understood that various modifications can be made to the embodiments disclosed herein without departing from the spirit and scope of the present invention, which should be determined from the appended claims. For example, instead of including an aseptic solution, the sanitary napkin device according to the present invention can employ an antiseptic topical solution, such as benzalconic chloride, boric acid, potassium permanganate etc., to kill existing microorganisms and detain their pullulation in the field of the live infected tissue. Furthermore, the sanitary napkin device according to the present invention can include a medicated topical solution, such as polyoximethylenourea, dymethicone, xylocaine; 9-amine hydrochloride acridine, etc.

Moreover, two or more towelettes containing the same or different topical solutions, whether asepticizing, antiseptic and/or medicated, can be included in the hermetic sheath. In such a case, sterilized impermeable sheets of, for example, polyethylene, are placed between the individual towelettes which need to be separated.

In addition, although the hermetic sheath described herein is intended to be torn and disposed of, a re-usable hermetic sheath can be used in the sanitary napkin device according to the present invention.

I claim:

1. A system for feminine hygiene comprising:
   a sanitary napkin having an impermeable protector, a permeable cover secured to said impermeable protector, and an absorbent pad positioned between said permeable cover and said impermeable protector;
   an area of adhesive positioned on said impermeable protector;
   a hermetic sheath releasably adhered to said area of adhesive;
   a member made of hydrophilic material sealed in said hermetic sheath; and
   an aseptic topical solution contained in the hydrophilic member.

2. The feminine hygiene system of claim 1, wherein said hermetic sheath includes means for opening said hermetic sheath to provide access to said hydrophilic member.

3. The feminine hygiene system of claim 1, wherein said hermetic sheath comprises two sheets of impermeable material sealed to one another in an area extending all around the periphery of the sheets.

4. The feminine hygiene system of claim 2, wherein said hermetic sheath comprises two sheets of impermeable material sealed to one another all around the periphery of the sheets, and said means for opening said sheath comprises a flap extending from each said sheet beyond the area of sealing, whereby the flaps can be grasped and pulled apart to open said sheath.

5. The feminine hygiene system of claim 1, wherein said hermetic sheath has an outer layer including means for enhancing the release of said hermetic sheath from said adhesive.

6. The feminine hygiene system of claim 5, wherein said release enhancing means comprises a silicone material.

7. The feminine hygiene system of claim 1, wherein said sanitary napkin has a generally trapezio-pyramidal shape.

8. The feminine hygiene system of claim 7, wherein said impermeable protector of said sanitary napkin has a generally trapezoidal shape having a wide end, a narrow end, non-parallel sides and a length extending perpendicularly between said wide end and said narrow end.

9. The feminine hygiene system of claim 8, wherein said area of adhesive comprises an adhesive strip extending along the length of said impermeable protector.

10. The feminine hygiene system of claim 9, wherein said hermetic sheath comprises means for reinforcing said sanitary napkin, whereby said sanitary napkin maintains its trapezio-pyramidal shape.

11. The feminine hygiene system of claim 1, wherein said aseptic topical solution comprises propylene glycol.

12. The feminine hygiene system of claim 11, wherein said aseptic topical solution comprises a 30% solution of propylene glycol in purified water.

13. The feminine hygiene system of claim 8, wherein said impermeable protector is generally concave, along its length, toward said permeable cover.

14. The feminine hygiene system of claim 8, wherein said permeable cover defines a top surface of said sanitary napkin, said top surface being convex in a direction transverse to the length of said sanitary napkin.

15. The feminine hygiene system of claim 7, wherein said sanitary napkin includes an orthocentral portion, said absorbent pad having a thickness which is a maximum in said orthocentral portion, a narrow portion which is narrower than the orthocentral portion and in which the thickness of said pad is slightly less than the thickness of the pad in the orthocentral portion, and a wide portion which is wider than the orthocentral portion and in which the thickness of the pad tapers from the orthocentral portion to a wide end of the sanitary napkin.

* * * * *

UNITED STATES PATENT AND TRADEMARK OFFICE
CERTIFICATE OF CORRECTION

PATENT NO. : 4,848,572

DATED : July 18, 1989

INVENTOR(S) : Patricio BELTRAN

It is certified that error appears in the above-identified patent and that said Letters Patent is hereby corrected as shown below:

TITLE PAGE under item [19], "Herrera" should be --Beltran-- and

[76] Inventor: should be --Patricio Beltran--.

Col. 2, line 53, change "towelette 16" to -- towelette 46 --;

line 67, change "tion 28" to -- tion 30 --;

line 68, change "tion 30" to -- tion 28 --.

Col. 4, line 39, change "30" to -- 28 --.

Col. 8, line 43, change "64, 66, 6" to -- 64, 66, 68 --.

Signed and Sealed this

Fourteenth Day of January, 1992

Attest:

HARRY F. MANBECK, JR.

*Attesting Officer*     *Commissioner of Patents and Trademarks*